United States Patent [19]

Brown

[11] Patent Number: 4,918,207

[45] Date of Patent: Apr. 17, 1990

[54] NOVEL OPTICALLY ACTIVE HALO-SUBSTITUTED TETRAHYDROFURANS

[75] Inventor: Herbert C. Brown, West Lafayette, Ind.

[73] Assignee: Aldrich Chemical Co., Inc., Milwaukee, Wis.

[21] Appl. No.: 364,874

[22] Filed: Jun. 12, 1989

Related U.S. Application Data

[62] Division of Ser. No. 175,178, Mar. 30, 1988.

[51] Int. Cl.$^4$ .................. C07D 307/02; C07D 307/06
[52] U.S. Cl. .................................................. 549/504
[58] Field of Search ................ 568/630, 661; 549/504, 549/404

[56] References Cited

U.S. PATENT DOCUMENTS

| | | | |
|---|---|---|---|
| 3,901,927 | 8/1975 | Seeger et al. | 549/504 |
| 4,263,212 | 4/1981 | Hong | 568/661 |
| 4,397,864 | 8/1983 | Nakatani et al. | 568/661 |

FOREIGN PATENT DOCUMENTS 0169683  12/1981  Japan .................. 549/504

*Primary Examiner*—Werren B. Lone
*Attorney, Agent, or Firm*—Niblack & Niblack

[57] ABSTRACT

A process for producing the optically pure (+)- or (−) isomer of a pheynl- or substituted- phenylalkanolamine compounds having pharmacologic activity without the need for resolution processes and novel intermediates useful in the process including optically pure haloalcohols are provided.

9 Claims, No Drawings

NOVEL OPTICALLY ACTIVE HALO-SUBSTITUTED TETRAHYDROFURANS

This is a division of application Ser. No. 175,178 filed Mar. 30, 1988.

BACKGROUND OF THE INVENTION

A. Field of Invention

The present invention relates to an improved process for producing phenyl- or substituted-phenylalkanolamine compounds having pharmacologic activity and to novel intermediates useful in the process, and more particularly relates to a process for directly obtaining the desired (+)- or (−) enantiomer in essentially 100% ee (enantiomeric excess) without the need for tedious resolutions.

Many biologically active compounds and medicinals are synthesized as racemic mixtures However, commonly, only one of the optical isomers has the desired properties, while the other may possess only very weak or a different, undesired pharmacological activity, or at worst, is toxic. This problem is best illustrated by the problems associated with Thalidomide which was unfortunately marketed as a racemic mixture of the toxic isomer, responsible for the well-publicized birth defects, as well as the active optical isomer which was free from the teratological side effects. The Thalidomide tragedy could have been avoided had there been a simple, economical process available for separating the isomers. Since then, the pharmaceutical industry has employed tedious and expensive resolution processes to insure that only the desired optical isomer is present in the finished formulation. It is therefore highly desirable for the pharmceutical industry to be able to obtain one enantiomer in a simple, direct, less costly process.

Many pharmaceutically active compounds are phenyl-or substituted-phenylalkanolamines having the basic structure

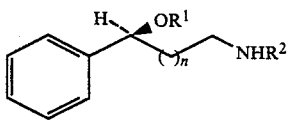

wherein n is 1 or 2, $R^1$ is hydrogen, acetoxy, phenyl or substituted phenyl and $R^2$ is lower alkyl, phenyl or substituted phenyl.

Typical drugs of this kind include Isoproternol, Colterol, phenylephrine, Bitolerol, Dipeverfrin, and the major new anti-depressent agents, Tomoxetine, Fluoxetine and Nisoxetine.

Tomoxetine, [[R]-(−)-N-methyl- -(2-methylphenoxy)-benzenepropamine hydrochloride, Eli Lilly, and Company, LY 139603] is a new drug currently undergoing investigation as an antidepressant (R. L. Zerbe et al., *J. Pharmacol. Exp. Ther.* 1985, 232, 139). The (−)-optical isomer has been shown to be nine times more potent than the (+)-isomer. Unlike chemical tricyclic antidepressants such as imipramine, (−)-Tomoxetine has been shown to inhibit specifically norepinephrine uptake in humans at dosages which are clinically well tolerated and to be a relatively weak ligand for $\alpha$-1, $\alpha$-2 and $\beta$-adrenergic receptors. The latter receptors are generally regarded as responsible for undersirable side-effects associated with antidepressants.

The patent literature preparation of (−)-Tomoxetine involves a long and tedious procedure culminating in a highly inefficient resolution (20%) of the racemic mixture. See Molly et al. U.S. Pat. No. 4,018,895 and Foster et al. Eur. Patent No. 0052492. Clearly, an enantiomeric preparation of (−)-Tomoxetine is needed. The best procedure to date provides an overall yield of the (−)-isomer of 14% and an optical purity of only 88% ee. The present invention provides a simple synthesis of both (−)-Tomoxetine, (+)-Tomoxetine in essentially 100% ee, as well as both optically pure enantiomers of the cognant compounds, Fluoxetine and Nisoxetine.

In general, many of these valuable drugs in addition to the Lilly antidepressants discussed above are synthesized via the Mannich reaction to produce the amino substituted arylalkyl ketone. Reduction of the ketone gives the alcohol. The mixture of enantiomeric arylalkanolamines are then resolved in a generally tedious, costly inefficient process.

Thus, there exists a need for a more efficient, cost effective, simple process for directly obtaining the desired isomer of Tomoxetine and other arylalkanolamine pharmaceutical agents in essentially 100% enantiomeric excess. The present invention provides such a process as well as valuable intermediates useful in such process.

B. Prior Art

Recently, it was discovered that diisopinocamphylchloroborane, hereafter Ipc$_2$BCl, derived from either (+)- or (−)-alpha-pinene is capable of reducing arylalkyl ketones to the corresponding alcohols in a highly enantioselective fashion. (Brown et al., *J. Org. Chem.* 1985, 50, 5446. See also Herbert C. Brown copending U.S. patent application Ser. No. 902,175 filed Aug. 29, 1986). The alcohols so obtained were simple compounds, containing no other functionality, and as such were end-products in themselves. However, for the construction of more complex molecules, often required of biologically active compounds, additional functionalities that can be further transformed are desirable. The halides are a particularly appealing functional group.

Chiral haloalcohols have been prepared in variable enantiomeric excess with a reagent developed by Itsuno et al. (*J. Chem. Soc.* Perkin Trans. I. 1985, 2615). In addition to inconsistant optical yields, the nature of the reagent remains in doubt. Soai et al. (*J. Chem. Soc. Chem. Comm.* 1986, 1018) have demonstrated that a chirally modified lithium borohydride can reduce betahalogenoketones in 81–87% ee. More consistent results have been obtained for asymmetric reduction of 2-haloacetophenones with neat Alpine-Borane (Brown et al, *J. Org. Chem.* 1985, 50, 1384).

In my copending application Ser. No. 902,175, filed Aug. 29, 1986, I disclosed that diisopinocampheylhaloboranes (Ipc$_2$BX) are exceptionally effective asymmetric reducing agents for simple phenylketones to the corresponding alcohol. The reagents Ipc$_2$BX appear to be the most effective currently available for such asymmetric reductions, and one would expect that reduction of the arylalylketoamines should provide a direct route to the desired optically pure arylalkylaminoalcohols. Unfortunately, the presence of the amino groups prevents the desired reaction. Tertiary amines coordinate with Ipc$_2$BX to prevent its use for reduction. Primary and secondary amines react to give the amino-substituted boron compounds RNHBIpc$_2$+HX.

The present invention provides a solution to that problem by providing a method in which the Ipc$_2$BX reagents are used to reduce a halo-substituted arylalkylketone. Treatment of the haloaralkylalcohol with the appropriate amine gives the desired optically pure arylalkylaminoalcohol.

The present invention also fulfulls the need for a simple, reliable method of preparing each enantiomer of structurally diverse, optically pure haloalcohols at will, which are intermediates in the preparation of optically pure phenoxyhalides which are useful as intermediates in the synthesis of the optically pure, desired enantiomer of a pharmaceutically active phenyl- or substituted-phenylalkanolamine.

SUMMARY OF THE INVENTION

In one embodiment, the present invention provides an improved, simple, cost effective method of directly producing either optical isomer of a pharmaceutically active arylalkanolamine represented by the formula

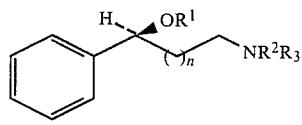

wherein $R^1$ is phenyl or substituted phenyl, n is an integer from 0 to 10 and $R^2$ and $R^3$ each are hydrogen or lower alkyl, in essentially 100% ee without the need for resolution as well as novel optically active intermediates useful in said process.

Generally speaking, the process of this invention, comprises the steps of reducing a halo-substituted phenylalkylketone with optically pure (—)- or (+)-Ipc$_2$BX to obtain the corresponding optically pure alcohol, and treating the alcohol with the appropriate amine to provide the desired optically pure (+)- or (—)-arylalkylaminoalcohol.

The following reaction scheme summarizes the process of the preferred embodiments of this invention.

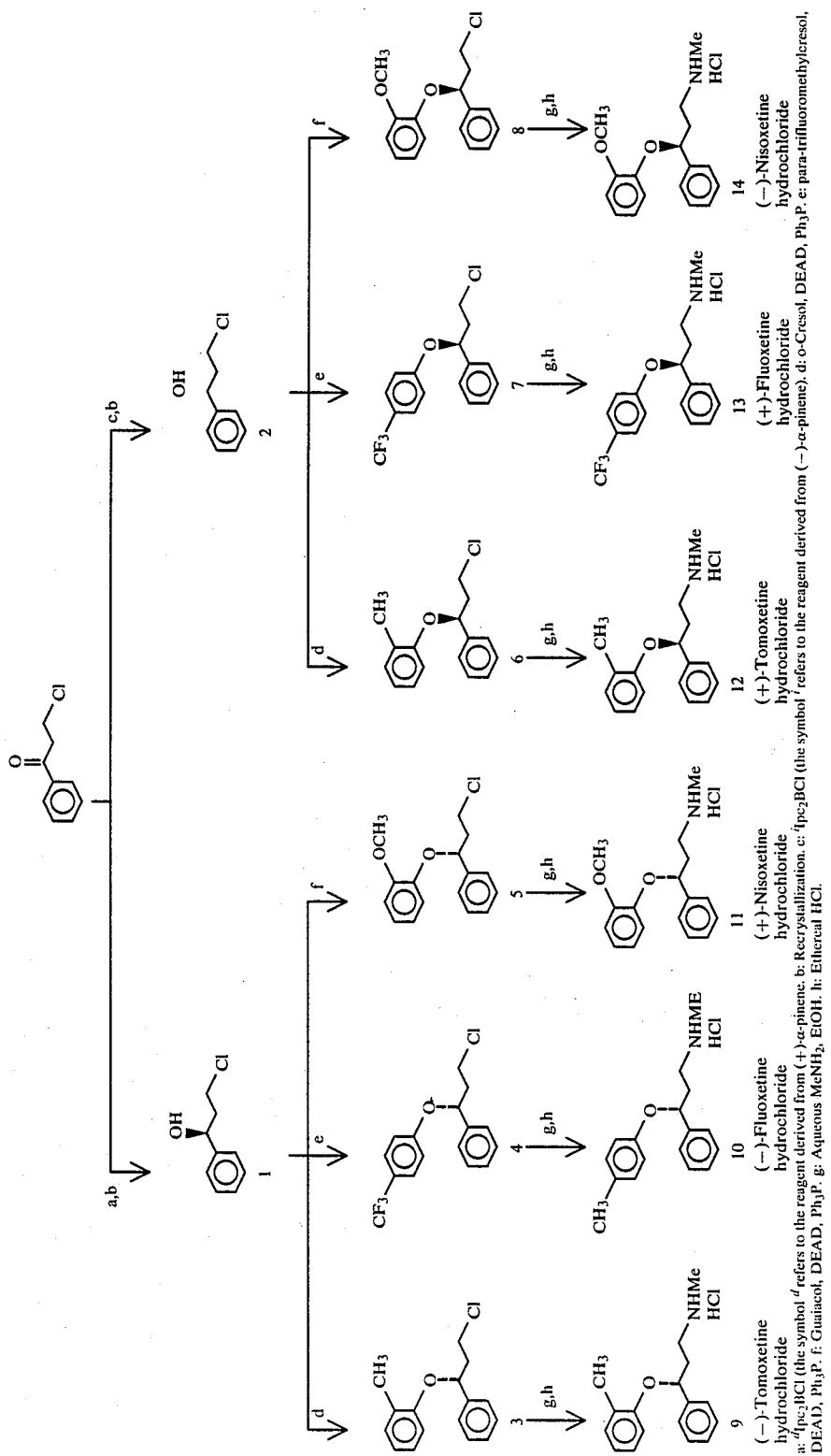

While in the preferred embodiment, the process of this invention is employed in the synthesis of either optically pure isomer of Tomoxetine hydrochloride and related anti-depressants, Nisoxetine hydrochloride and Fluoxetine hydrochloride, it can be used to synthesize essentially any arylalkylaminoalcohol in optical purities of essentially 100% ee by simply adjusting the starting materials and the amine employed in the reaction, as will be readily apparent to one skilled in the art.

In another embodiment, the present invention provides novel haloalcohols of essentially 100% ee represented by the formula

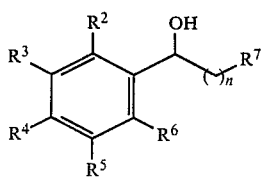

wherein each R is the same or different member of the group consisting of fluoro, chloro, bromo or iodo.

As used herein, the term "essentially 100% ee" or "high state of optical purity" refers to an enantiomeric excess of >95%, as determined by any analytical technique, i.e. gas chromotography, proton magnetic resonance, etc., on the derivatized or underivatized alcohols.

The term "lower alkyl", as used herein, refers to straight or branched chain alkyl groups having from 1 to 8 carbon atoms, inclusive, i.e., methyl, ethyl, n-propyl, iso-propyl, n-butyl, isobutyl, n-pentyl, 2-methylbutyl, 2,2-dimethylpropyl, n-hexyl, 2-methylpentyl, 2,2-dimethylbutyl, 2,3-dimethylbutyl, n-heptyl, 2-methylhexyl, 2,3-dimethylpentyl, 2,4-dimethylpentyl, n-octyl, 2-methylhexyl, 2,3-dimethylheptyl, and the like.

The term "substituted phenyl", as used herein, refers to a phenyl group represented by the forumula:

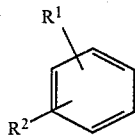

wherein R1 and R2 are the same or different members of the group consisting of hydrogen, loweralkyl or haloloweralkyl, with the limitation either $R_1$ or $R_2$ must be other than hydrogen.

The term "lower alkoxy" refers to an alkoxy group having from 1-8 carbon atoms, such as methoxy, ethoxy, propoxy, etc.

The term "halo lower alkyl" refers to a lower alkyl group as defined about containing from 1-4 halo substitutions, i.e., trifluoromethyl, 1,3-dichlorobutyl and the like.

The present invention also provides a method for converting 1,4-halohydrins of high optical purity to the corresponding tetrahydrofurans in which the optical purity of the alcohol is retained in the cyclized products of the following general structure in which one enantiomer is arbitrarily depicted.

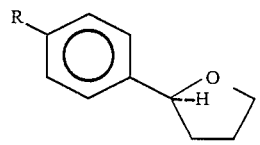

wherein R is halo (fluoro, chloro, bromo or iodo).

In addition, the present invention provides novel chiral 1,3-phenoxychlorides following general formula in which one enantiomer is arbitrarily drawn.

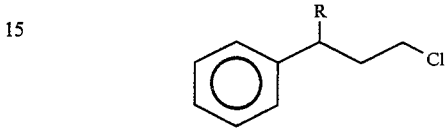

wherein R is lower alkyl, haloloweralkyl or loweralkoxy. The 1,3-phenoxychlorides of this invention are intermediates in the preparation of the corresponding 1,3-phenoxyamines or their salts with complete retention of optical activity. The 1,3-phenoxyamines are represented by the formula

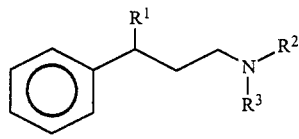

wherein $R^1$ is phenoxy substituted with lower alkyl, haloloweralkyl or loweralkoxy, $R^2$ is hydrogen or lower alkyl and $R^3$ is hydrogen or loweralkyl, or a pharmaceutically acceptable salt thereof.

Representative 1,3-phenoxypropylamines include Tomoxetine, Nisoxetine and Fluoxetine.

In a preferred embodiment, the haloalcohols of this invention are prepared by reacting diisopinocampheylchloroborane, $Ipc_2BCl$, with both ring and chain substituted haloarylketones to the corresponding haloalchols in excellent enantiomeric exess (95% or better). In most cases, simple recrystallization provides the pure enantiomers. The chiral haloalcohols of the present invention are highly versatile intermediates. They can be readily cyclized to oxiranes and 2-substituted tetrahydrofurans with retention of chirality. Using this methodology, the present invention provides an efficient, highly enantioselective synthesis of both optical isomers of the antidepreseent drugs Tomoxetine, Fluoxetine and Nisoetine, from the antipodal intermediates, (+)- or (−)-3-chloro-1-phenyl-1-propanol.

DETAILED DESCRIPTION OF PREFERRED EMBODIMENTS

The following examples further illustrate the present invention. Unless otherwise specified, all operations with organoboranes were performed under nitrogen. Melting points and boiling points are uncorrected. $^{13}C$ NMR spectra were obtained on a Varian FT-80A spectrometer (20.00 MHz) relative to TMS. GC analysis was done on a Hewlett-Packard 58902 gas chromatograph-mass spectrometer Model 4000. Optical rotations were recorded on a Rudolph Polarimeter Autopol III and were obtained at 23° C. unless otherwise specified. Reduction of ketones were carried out as described in the literature, by Chandrasekharan, J.; Ramachandran, P. V. and Brown, H. C., *J. Org. Chem.* 1985 50, 5446 and Brown, H. C.; Chandrasekharan, J.; Ramachandran, P. V., *J. Am. Chem. Soc.* 1988 110, 0000.

Tetrahydrofuran (Fisher), THF, was distilled from benzophenone ketyl and stored under nitrogen in an ampule. Diethyl ether (Mallincrodt), ethyl acetate (Mallincrodt), dichloromethane (Mallincrodt), pentane (Phillips), and hexane (Fisher) were used as received. Anhydrous ethereal hydrogen chloride was prepared from hydrochloric acid and sufuric acid using a Brown gasimeter. (Brown, H. C.; Kramer, G. W.; Levy, A. B.; Midland, M. M. "Organic Synthesis via Boranes", :Wiley Interscience: New York, 1975). o-Cresol,-α, α, α-trifluoro-p-cresol, guaiacol, triphenylphosphine, diethylazodicarboxylate and aqueous methylamine were purchased from the Alrdich Chemical Company. Reactions were monitored where ever possible by TLC using Whatman precoated silica plates. Neutral alumina (J. T. Baker & Company, Column Chromatography) was used for column chromatography.

The enantiomeric excess, ee, of the haloalcohols was determined by conversion to the MTPA esters, followed by analysis on a Methyl Silicone column (50 m) or Supelcowax column (15 m). In all cases, racemic alcohols gave baseline separations and 1:1 ratios of integrated areas.

EXAMPLE 1

[S]-(−)-1-chloro-3-phenyl-3-propanol

A solution of 3-chloropropiophenone (8.93 50 mmol in 25 ml THF) was added to (−) diisopinocampheylchloroborane (Ipc$_2$BCl, 18.0 g, 56 mmole, in 25 ml THF at −24° C.). The reaction was complete within 7 hours after which all volatiles were removed under reduced pressure. The residue was dissolved in ether, and diethanolamine (2 equivalents) was added. The resulting suspension was stirred for two hours and filtered. The solid residue was washed with ether and the combined washings and filtrate were concentrated. Distillation furnished [S]-(−)-1-chloro-3-phenyl-3-propanol. Yield: 6.1 g, 72%; mp 56°–57° C.; [α]$_D^{23}$ −25.25, c=7.05, CHCl$_3$; 97% ee.

EXAMPLE 2

[R]-(+)-1-Chloro-3-phenyl-2-propanol

[R]-(+)-1-Chloro-3-phenyl-2-propanol was prepared by the method of example 1 except that (+)-diisopinocampheylchloroborane was used. [α]$_D^{23}$ +25.3, c=7.05, CHCl$_3$; 97% ee.

EXAMPLES 3–28

The following novel optically active haloalcohols were prepared following the methods of Examples 1 and 2 by reduction of the appropriate prochiral haloketone with (−)- or (+)-diisopinocampheylchloroborane:

| Example | Compound |
|---|---|
| 3 | [S]-1-(2-bromophenyl)-1-ethanol |
| 4 | [R]-1-(2-bromophenyl)-1-ethanol |
| 5 | [S]-1-(4-bromophenyl)-1-ethanol |
| 6 | [R]-1-(4-bromophenyl)-1-ethanol |
| 7 | [S]-1-(4-chlorophenyl)-1-butanol |
| 8 | [R]-1-(4-chlorophenyl)-1-butanol |
| 9 | [S]-1-chloro-2-(2,4-dichlorophenyl)-2-ethanol |
| 10 | [R]-1-chloro-2-(2,4-dichlorophenyl)-2-ethanol |
| 11 | [S]-1-chloro-4-(4-bromophenyl)-4-butanol |
| 12 | [R]-1-chloro-4-(4-bromophenyl)-4-butanol |
| 13 | [S]-1-(3-fluorophenyl)-1-ethanol |
| 14 | [R]-1-(3-fluorophenyl)-1-ethanol |
| 15 | [S]-1-(4-fluorophenyl)-1-ethanol |
| 16 | [R]-1-(4-fluorophenyl)-1-ethanol |
| 17 | [S]-1-(2,4-difluorophenyl)-1-ethanol |
| 18 | [R]-1-(2,4-difluorophenyl)-1-ethanol |
| 19 | [S]-1-(2,5-difluorophenyl)-1-ethanol |
| 20 | [R]-1-(2,5-difluorophenyl)-1-ethanol |
| 21 | [S]-1-(2,6-difluorophenyl)-1-ethanol |
| 22 | [R]-1-(2,6-difluorophenyl)-1-ethanol |
| 23 | [S]-1-(3,4-difluorophenyl)-1-ethanol |
| 24 | [R]-1-(3,4-difluorophenyl)-1-ethanol |
| 25 | [S]-1-chloro-2-(4-fluorophenyl)-2-ethanol |
| 26 | [R]-1-chloro-2-(4-fluorophenyl)-2-ethanol |
| 27 | [S]-1-chloro-4-(4-fluorophenyl)-4-butanol |
| 28 | [R]-1-chloro-4-(4-fluorophenyl)-4-butanol |

Table I summarizes the above representative novel optically active haloalcohols of the present invention which are represented by Formula I.

TABLE I

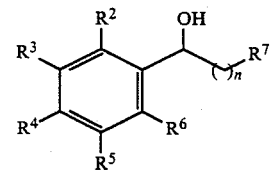

| $R_2$ | $R^3$ | $R^4$ | $R^5$ | $R^6$ | $R^7$ | n | % ee | abs. config |
|---|---|---|---|---|---|---|---|---|
| Br | H | H | H | H | H | 1 | 99 | S |
| Br | H | H | H | H | H | 1 | 99 | R |
| H | H | Br | H | H | H | 1 | 97 | S |
| H | H | Br | H | H | H | 1 | 97 | R |
| H | H | H | H | H | Cl | 3 | 98 | S |
| H | H | H | H | H | Cl | 3 | 98 | R |
| Cl | H | Cl | H | H | Cl | 1 | 95 | S |
| Cl | H | Cl | H | H | Cl | 1 | 96 | R |
| H | H | Br | H | H | Cl | 3 | 98 | S |
| H | H | Br | H | H | Cl | 3 | 98 | R |
| H | F | H | H | H | H | 1 | 96 | S |
| H | F | H | H | H | H | 1 | 96 | R |
| H | H | F | H | H | H | 1 | 97 | S |
| H | H | F | H | H | H | 1 | 97 | R |
| F | H | F | H | H | H | 1 | 96 | S |
| F | H | F | H | H | H | 1 | 96 | R |
| F | H | H | F | H | H | 1 | 96 | S |
| F | H | H | F | H | H | 1 | 96 | R |
| F | H | H | H | F | H | 1 | 96 | S |
| F | H | H | H | F | H | 1 | 96 | R |
| H | F | F | H | H | H | 1 | 95 | S |
| H | F | F | H | H | H | 1 | 95 | R |
| H | H | F | H | H | Cl | 3 | 98 | S |
| H | H | F | H | H | Cl | 3 | 98 | R |

In the above examples, the S isomer was obtained from (−)-Ipc$_2$BCl and the R isomer was obtained from (+)-Ipc$_2$BCl. All reductions were performed in THF at approximately 2M. The % ee was determined as the (+)-MTPA ester.

EXAMPLES 29–46

Following the process of Example I, the following haloalcohols are prepared from the corresponding haloketone and either (−)- or (+)-diisopinocampheylchloroborane:

| Example | Compound |
|---|---|
| 29 | [S]-(−)-1-iodo-3-phenyl-2-propanol |
| 30 | [R]-(+)-1-iodo-3-phenyl-2-propanol |
| 31 | [S]-1-(2-iodophenyl)-1-ethanol |
| 32 | [R]-1-(2-iodophenyl)-1-ethanol |
| 33 | [S]-1-(4-iodophenyl)-1-ethanol |
| 34 | [R]-1-(4-iodophenyl)-1-ethanol |
| 35 | [S]-1-(4-iodophenyl)-1-butanol |
| 36 | [R]-1-(4-iodophenyl)-1-butanol |
| 37 | [S]-1-iodo-2-(2,4-dichlorophenyl)-2-ethanol |
| 38 | [R]-1-iodo-2-(2,4-dichlorophenyl)-2-ethanol |
| 39 | [S]-1-iodo-4-(4-bromophenyl)-4-butanol |
| 40 | [R]-1-iodo-4-(4-bromophenyl)-4-butanol |
| 41 | [S]-1-(3-fluorophenyl)-1-pentanol |
| 42 | [R]-1-(3-fluorophenyl)-1-pentanol |
| 43 | [S]-1-(4-iodophenyl)-1-octanol |
| 44 | [R]-1-(4-fluorophenyl)-3-propanol |
| 45 | [S]-1-(2,4-difluorophenyl)-3-propanol |
| 46 | [R]-1-(2,4-diiodo-1-hexanol) |

The novel optically active tetrahydrofurans of the present invention are represented by Formula II

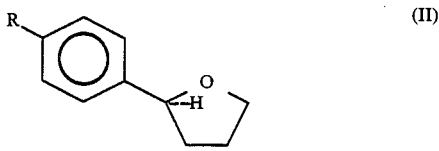

wherein R is halo. The preparation of the optically active tetrahydrofurans of this invention are illustrated in Examples 47–50.

EXAMPLE 47

[S]-2-(4-bromophenyl)-tetrahydrofuran

A solution of [S]-1-chloro-4-(4-bromophenyl)-4-butanol (50 mmol) in THF (25 ml) was added to a cooled suspension (0° C.) of NaH (55 mmol) in THF (50 ml). After being stored for 2 h at 25C, the reaction mixture was quenched with water, brought to pH 6 with concentrated HCl, and extracted with ether (2×50 ml). The organic phase was dried over $H_2SO_4$, filtered and all volatiles removed under reduced pressure. The residue was distilled to provide the product in 75% yield, 98% ee as determined on a chiral capillary column of Ni(HFN-IR-Cam)$_2$.

EXAMPLES 48–50

The following representative optically active 2-substituted tetrahydrofurans were prepared by the method of Example 47 from the corresponding optically active haloalcohol.

| Example | Compound | % ee |
|---|---|---|
| 48 | [S]-2-(4-fluorophenyl)-tetrahydrofuran | 98 |
| 49 | [R]-2-(4-fluorophenyl)-tetrahydrofuran | 98 |
| 50 | [R]-2-(4-bromophenyl)-tetrahydrofuran | 98 |

EXAMPLES 51–54

The following representative are also prepared following the method of Example 47: [S]-2-(4-iodophenyl)-tetrahydrofuran; [R]-2-(4-iodophenyl)-tetrahydrofuran; [S]-2-(4-chlorophenyl)-tetrahydrofuran; and [R]-2-(4-chlorophenyl)-tetrahydrofuran.

The 1,3-halohydrins of Formula I are converted to novel 1,3-phenoxyhalides represented by Formula III below which are important intermediates in the preparation of biologically active propylamines. The novel optically active 1,3-phenoxychlorides of the present invention are presented by the formula:

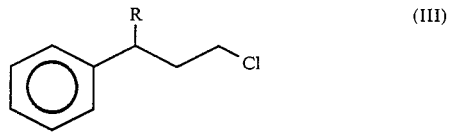

wherein R is phenoxy substituted by lower alkyl, loweralkoxy or haloloweralkyl. The preparation of representative 1,3-phenoxychlorides is described in the following examples.

EXAMPLE 55

[R]-(−)-1-Chloro-3-phenyl-3-(2-methylphenoxy)propane

Triphenylphosphine (5.25 g, 20 mmol) and ethylazodicarboxylate (3.15 ml, 3.48 g, 20 mmol) were added to a solution of [S]-1-chloro-3-phenyl-3-propanol (3.4g, 20 mmol) and cresol (2.06 ml, 2.16 mmol) in THF (50 ml). The mixture was stirred at room temperature overnight until the reaction was complete as determined by TLC. THF was removed under aspirator vacuum and the residue treated with pentane (3×50 ml). The combined pentane fractions were concentrated and the residue chromatographed on neutral alumina. Elution with pentane and removal of solvent afforded 3.6 g (70% yield) of the chloro ether as a thick liquid which was found to be 99% pure by gas chromatograph. Bp 180°–200° C./0.5 mm; $[\alpha]_D^{23}$ −21.7° (c 3.9, $CHCl_3$); $^{13}$C-NMR :150.67, 147.81, 128,76, 127,98, 125.32, 122.23, 120.96, 117.35, 112.71, 59.02, 56.02, 41.61. Mass spectrum (EI): 260/262 (1,M+), 224 (1, M+-HCl), 153 (21, M+-$C_7H_8O$), 91 (100, $C_7H_7$). (CI): 261 (7.4, M+ +H), 153/155 (100, M+ +H-$C_7H_8$).

EXAMPLE 56

[R]-(−)-Tomoxetine Hydrochloride

To the chloroether of Example 55 (2.6 g, 10 mmol) in a Paar "mini-reactor" was added aqueous methylamine (40%, 20 ml). Ethanol (10 ml) was added as a cosolvent and the solution heated at 30° C. for 3 hours. The solution was cooled to room temperature and the mixture was poured on water (150 ml) and extracted with ether. The ether extract was washed with water, brine and dried over $MgSO_4$. HCl in EE (5 ml of 3.2 M, 16 mmol) was added to the decanted solution.

EXAMPLE 57

[S]-(+)-1-Chloro-3-phenyl-3-(2-methylphenoxy)propane

This chloroether was prepared following the method of Example 55, using [R]-3-chloro-1-phenylpropanol (3.4 g, 20 mmol), o-cresol (2.06 ml, 20 mmol), triphenylphosphine (5.25 g, 20 mmol) and diethylazodicarboxylate (3.15 ml, 20 mmol) in THF (50 ml). Workup yielded the title compound (3.5 g, 68%) as a thick liquid, bp 180°–200° C./0.5 mm; $[\alpha]_D^{+21.7}$ (c 3.9, $CHCl_3$); $^{13}$C NMR and the mass spectra were identical to the [R]-(−)-isomer of Example 55.

EXAMPLE 58

[S]-(+)-Tomoxetine Hydrochloride

[S]-Tomoxetine hydrochloride was prepared using the same procedure as for the preparation of the [R]-(−)-isomer from the chloroether of Example 57 and excess aqueous methylamine in a "minireactor" at 130° C. for 3 hours. Workup provided the optically pure [S]-(+)-isomer in 95% yield, $[\alpha]_D^{23}$ +42.9° (c 6, MeOH). All spectral data are identical to [R]-(−)-Tomoxetine hydrochloride. Anal. Calcd. for $C_{17}H_{22}ClNO$: C, 69.98; H, 7.55; Cl, 12.18; N, 4.9. Found: C, 69.1; H, 7.9; Cl, 12.29; N, 4.91.

EXAMPLE 59

[R]-(+)-1-chloro-3-phenyl-3-(4-trifluoromethylphenoxy)propane

The title compound was prepared by the method of example 55 using [S]-3-chloro-1-phenylpropanol (2.57g, 15 mmol), α,α,α-trifluorocresol (2.4 g, 15 mmol) in THF (40 ml) at room temperature. Workup provided the optically pure title compound as a thick liquid, bp 180°-200° C./0/5 mm. $[\alpha]_D$+2.3° (c 10, CHCl$_3$; $^{13}$C NMR (CDCl$_3$): 140.50, 129.39, 128.66, 127,56, 127.38, 127.19, 127.01, 126.34, 116.45, 77.82, 41.69, 41.38. Mass spectrum (EI): 153/155 (45), 91 (100). (CI): 314/316, (1, M+), 153/155 (100). Anal. Calcd. for $C_{16}H_{14}ClNO$: C, 61.05; H, 4.45; Cl, 11.29; F, 18.12. Found: C, 61.06; H, 4.51; Cl, 11.16; F, 18.22.

EXAMPLE 60

[R]-(−)-Fluoxetine Hydrochloride

[R]-(−)-Fluoxetine hydrochloride was prepared following the procedure of Example 56 for [R]-(−)-Tomoxetine hydrochloride utilizing [R]-(+)-1-chloro-3-phenyl-3-(trifluoromethylphenoxy)propane (Example 59) (1.57 g, 5 mmol) and excess aqueous methylamine in ethanol as cosolvent in a "minireactor" at 130° C. for 3 hours. Workup provided 1.55 g, 90% yield, of the recystallized, optically pure (CH$_2$Cl$_2$/EtOAc) [R]-(−)-Fluoxetine hydrochloride: mp 142°-143° C.; $[\alpha]_D^{22}$+3.01° (c 5.3, MeOH); $[\alpha]_D^{22}$ −15.52° (c 7.15, CHlC$_3$); $^{13}$C NMR (CDCl$_3$) 160.10, 139.46, 129.28, 128.66, 127.35, 127.16, 126.96, 126.77, 126.08, 116.26, 55.49, 46.32, 34.77, 33.13. Mass spectrum (EI): 44 (100, CH$_2$NHMe). (CI): 310 (100, M++H), 148 (12). Anal. calcd. for $C_{17}H_{19}ClF_3NO$: C, 59.05; H, 5.54; N, 4.05; F, 16.48; Cl, 10.25. Found: C, 59.02; H, 5.6; N, 4.13; F, 16.67; Cl, 10.5.

EXAMPLE 61

[S]-(−)-1-chloro-3-phenyl-3-(4-trifluoromethylphenoxy)propane

The title chloro ether was prepared from [R]-(+)-3-chloro-1-phenylpropanol (2.56g, 15 mmol), α,α,α-trifluoro-p-cresol (2.43g, 15 mmol), triphenylphospine (3.93g, 15 mmol) and diethylazodicarboxylate (2.36 ml, 15 mmol) in THF (40 ml) at room temperature. Workup provided the title compound as a thick liquid. Yield: 3.07 g, 65%, bp 180°-200° C./0.5 mm $[\alpha]_D$−2.2° (c 12.5, CHCl$_3$): $^{13}$C NMR and mass spectrum were identical to those of the [R]-(−) isomer of Example 59.

EXAMPLE 62

[S]-(+)-Fluoxetine Hydrochloride

[S]-(+)-Fluoxetine hydrochloride was prepared following the method of Example 60 from the chloro ether of Example 61 (1.59 g, 5 mmol) and excess aqueous methylamine in ethanol as cosolvent in a "mini-reactor" at 130° C. for 3 hours. Workup provided 1.55 g (95%) of the recystallized (CH$_2$Cl$_2$/EtOAc) optically pure title compound, mp 142°-143° C.: $[\alpha]_D^{22}$−3.04° (c 5.9, MeOH), $[\alpha]_D^{22}$+15.83° (c CHCl$_3$); $^{13}$C NMR (CDCl$_3$): 160.08, 139.44, 129.26, 128.64, 127.30, 127.12, 126.76, 116.25, 77.48, 46.32, 34.77, 33.14. Mass spectrum (EI): 44 (100, CH$_2$NHMe). (CI): 310 (100, M++H), 148 (12). Anal. calcd. for $C_{17}H_{19}ClF_3NO$: C, 59.05; H, 5.54; N, 4.05; F, 16.48; Cl, 10.25. Found: C, 58.70; H, 5.58; N, 4.29; F, 16.38; Cl, 10.35.

EXAMPLE 63

[R]-(+)-1-chloro-3-phenyl-3-2-methoxyphenoxy)propane

The title chloroether was prepared by the method of Example 55 using [S]-(−)-3-chloro-1-phenylpropanol (1.71 g, 10 mmol), guaiacol (1.1 ml, 10 mmol), Ph$_3$P (2.62 g, 10 mmol) and diethylazodicarboxylate (1.57 ml, 10 mmol) in THF (40 ml) at room temperature. Workup and chromatography with neutral alumina (hexane/ethyl acetate: 97.3) gave 1.7 g (62%) of the title compound as a thick liquid, bp 180°-200° C./0.5 mm. The liquid, upon cooling, solidified and was recrystallized from pentane, mp 59°-61° C. $[\alpha]_D$+40.96 (c 7.8, CHCl$_3$): $^{13}$C NMR (CdCl$_3$): 150.67, 147.81, 141.28, 128,76, 127.98, 126.32, 122.23, 120.96, 117.35, 112.71, 79.02, 56.07, 41.61. Mass spectrum (EI): 276/278 (1, M+), 240 (M+-HCl), 260/262 (M-CH$_4$), 91 (100), 124 (82). (CI): 277/279 (13.6, M++H), 153/155 (100). Anal. calcd. for $C_{17}H_{22}ClNO_2$: C, 69.44; H, 6.15; Cl, 12.84. Found: C, 69.67; H, 6.3; Cl, 12.65.

EXAMPLE 64

[R]-(+)-Nisoxetine hydrochloride

[R]-(+)-Nisoxetine hydrochloride was prepared from the chloroether of Example 63 (1.35 g, 5 mmol) and excess aqueous methylamine in ethanol (1 ml) in a "mini-reactor" at 130° C. for 3 hours. Workup gave 1.41 g ((91%) of recrystallized product (Ch$_2$Cl$_2$/EtOAc), mp 149°-150° C.; $[\alpha]_D$+51.88° (c 4.8, MeOH); $^{13}$C NMR: 150, 140.18, 129.29, 129.07, 128.58, 126.14, 123.03, 121.32, 117.29, 112.23, 81.83, 56.44, 47.56, 34.20, 33.19. Mass spectrum (EI): 167, 44 (100), 148 (8). (CI): 272 (100, M+). Anal. Calcd. for $C_{17}H_{22}ClNO_2$: C, 66.34; H, 7.15; N, 4.55; Cl, 11.5. Found: C, 66.08; H, 5.2; N, 4.66; Cl, 11.59.

EXAMPLE 66

[S]-(−)-Chloro-3-phenyl-3-(2-methoxyphenoxy)propane

The title chloroether was prepared in a manner similar to Example 64. Yield: 1.64 g (60%). Mp 59°-61° C.; $[\alpha]_D$−41.6 (c 3, CHCl$_3$); $^{13}$C NMR and mass spectrum were identical to the chloroether of example 64.

EXAMPLE 67

[S]-(−)-Nisoxetine Hydrochloride

[S]-(−)-Nisoxetine hydrochloride was prepared from [S]-(−)-chloro-3-phenyl-3-(2-methoxyphenoxy)propane by the method of Example 65 to yield 1.41 g (91%) of the optically pure product. Mp 149°–151° C.; [α]$_D$ −52° C. (c 5, MeOH). $^{13}$C NMR and mass spectra were idential to that of the [R]-(+)-isomer.

The conversion of optically active 1,3-phenoxychlorides to the corresponding 1,3-phenoxyamines with complete retention of optical activity has been illustrated in the above representative examples. The process of this invention is applicable as a general method for the preparation of any (+) or (−) Tomoxetine, Fluoxetine or Nisoxetine analog in 100% optical purity. Referring to the following general formula for such derivatives:

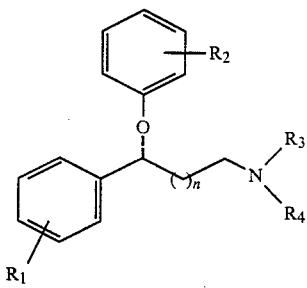

any substituent or substituents on the phenyl ring can be accomodated for reduction with Ipc$_2$BCl. Any chain length is also compatible with the process of this invention.

The process of this invention is also broadly applicable to the preparation of the desired, optically pure isomer of any aryalkanolamine pharmaceutical agent.

The invention claimed is:

1. A novel, optically active tetrahydrofuran of essentially 100% ee represented by the formula

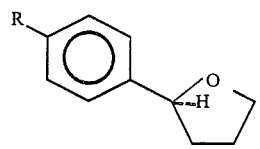

wherein R is halo selected from the group consisting of chloro, fluoro, bromo and iodo.

2. A compound of claim 1, [S]-2-(4-bromophenyl)-tetrahydrofuran.

3. A compound of claim 1, [R]-2-(4-bromophenyl)-tetrahydrofurna.

4. A compound of claim 1, [S]-2-(4-fluorophenyl)-tetrahydrofuran.

5. A compound of claim 1, [R]-2-(4-fluorophenyl)-tetrahydrofuran.

6. A compound of claim 1, [S]-2-(4-iodophenyl)-tetrahydrofuran.

7. A compound of claim 1, [R]-2-(4-iodophenyl)-tetrahydrofuran.

8. A compound of claim 1, [S]-2-(4-chlorophenyl)-tetrahydrofuran.

9. A compound of claim 1, [R]-2-(4-chlorophenyl)-tetrahydrofuran.

* * * * *

UNITED STATES PATENT AND TRADEMARK OFFICE
CERTIFICATE OF CORRECTION

PATENT NO. : 4,918,207           Page 1 of 11

DATED : April 17, 1990

INVENTOR(S) : Herbert C. Brown

It is certified that error appears in the above-identified patent and that said Letters Patent is hereby corrected as shown below:

ON THE TITLE PAGE
IN THE ABSTRACT

Line 2, "pheyn" should read --phenyl--.

Line 5, "haloal-" should read --haloalcohols--.

Line 6, "cohols" should be deleted.

Column 1, line 11, "phenylalkanola-" should read --phenylalkanol--

Column 1, line 12, "mine" should read --amine--.

Column 1, line 19, there should be a period --.-- after "mixtures".

Column 1, line 38, delete "phe-"

Column 1, line 39, "nyl" should read --phenyl--.

Column 1, line 55, "methylphenox" should read --methylphenoxy--.

Column 1, line 56, delete "y".

UNITED STATES PATENT AND TRADEMARK OFFICE
CERTIFICATE OF CORRECTION

PATENT NO. : 4,918,207
DATED : April 17, 1990
INVENTOR(S) : Herbert C. Brown

It is certified that error appears in the above-identified patent and that said Letters Patent is hereby corrected as shown below:

Column 2, line 32, "1985" should be in bold print.

Column 2, line 44, "inconsistant" should read --inconsistent--.

Column 2, line 59, "arylalylketoamines" should read --arylalkylketoamines--.

Column 2, line 64, "sub" should be deleted.

Column 2, line 65, "stituted" should read --substituted--.

Column 2, line 68, "arylalk-" should read --arylalkyl- --.

Column 3, line 1, "ylketone" should read --ketone--.

Column 3, line 2, "ary-" should be deleted.

Column 3, line 3, "lalkylaminoalcohol" should read --arylalkylaminoalcohol--.

UNITED STATES PATENT AND TRADEMARK OFFICE
CERTIFICATE OF CORRECTION

PATENT NO. : 4,918,207
DATED : April 17, 1990
INVENTOR(S) : Herbert C. Brown

It is certified that error appears in the above-identified patent and that said Letters Patent is hereby corrected as shown below:

Column 3, lines 1-21 were double spaced during printing and should be single spaced with the text on Column 4 immediately following.

Column 6, Formula 10, "$CH_3$" should read --$CF_3$--.

Column 6, Formula 10, NHME" should read --NHMe--.

Column 7, line 36, "2-methylbu" should read --2-methylbutyl--.

Column 7, line 37, delete "tyl".

Column 7, line 59, "about" should read --above--.

Column 8, lines 1-8, in the formula, the furan ring should be closed to read as follows:

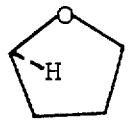

UNITED STATES PATENT AND TRADEMARK OFFICE
CERTIFICATE OF CORRECTION

PATENT NO. : 4,918,207
DATED : April 17, 1990
INVENTOR(S) : Herbert C. Brown

It is certified that error appears in the above-identified patent and that said Letters Patent is hereby corrected as shown below:

Column 8, line 43, "haloal" should read --haloalcohols--.

Column 8, line 44, "chols" should be deleted.

Column 8, line 53, "Nisoetine" should read --Nisoxetine--.

Column 9, line 2, "50" should be italicized.

Column 9, line 4, "110" should be italicized.

Column 9, line 57, "haloket" should read --haloketone--.

Column 9, line 58, "tone" should be deleted.

Column 11, lines 23-30, in Formula II, the furan ring was left open in printing. The ring should contact the "O" to read as follows:

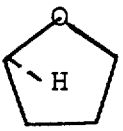

UNITED STATES PATENT AND TRADEMARK OFFICE
CERTIFICATE OF CORRECTION

PATENT NO. : 4,918,207

DATED : April 17, 1990

INVENTOR(S) : Herbert C. Brown

It is certified that error appears in the above-identified patent and that said Letters Patent is hereby corrected as shown below:

Column 11, line 64, "tetrahy" should read --tetra- --.

Column 11, line 65, "drofuran" should read --hydrofuran--.

Column 12, line 20, "pro" should read --propane--.

Column 12, line 36, the "c" in (c 3.9) should be underlined.

Column 12, line 20, "pane" should be deleted.

Column 12, line 25, "cresol" should read --o-cresol.

Column 12, line 37, "128,76" should read --128.76--.

Column 12, line 37, "125,98" should read --125.98.

Column 12, line 57, "pro-" should read --propane--.

Column 12, line 58, "pane" should be deleted.

Column 12, line 61, the "o" in "o-cresol" should be underlined.

UNITED STATES PATENT AND TRADEMARK OFFICE
CERTIFICATE OF CORRECTION

PATENT NO. : 4,918,207

DATED : April 17, 1990

INVENTOR(S) : Herbert C. Brown

It is certified that error appears in the above-identified patent and that said Letters Patent is hereby corrected as shown below:

Column 12, line    the "c" in "(c 3.9" should be underlined.

Column 13, line 10, the "c" in "(c 6" should be underlined.

Column 13, line 18, "phenox" should read --phenoxy)--.

Column 13, line 19, "Y)propane" should read --propane--.

Column 13, line 25, the "c" in "(c 10" should be underlined to read --(c 10--.

Column 13, line 46, the "c" in "(c 5.3" should be underlined to read --(c 5.3".

Column 13, line 46, the "c" in "(c 7.15" should be underlined to read --(c 7.15--.

UNITED STATES PATENT AND TRADEMARK OFFICE
CERTIFICATE OF CORRECTION

PATENT NO. : 4,918,207

DATED : April 17, 1990

INVENTOR(S) : Herbert C. Brown

It is certified that error appears in the above-identified patent and that said Letters Patent is hereby corrected as shown below:

Column 13, line 57, "4-trifluoromethylphenox" should read --4-trifluoromethylphenoxy--.

Column 13, line 58, in the second line of the title of Example 61:

a) remove the bold print which was introduced during printing as were the vast majority of the errors enumerated herein;

b) "y(propane)" should read --propane--.

Column 13, line 62, the "p" in "fluoro-p-cresol" should be underlined.

Column 13, line 66, the "c" in "(c 12.5" should be underlined.

Column 14, line 11, the "c" in "(c 5.9" should be underlined.

Column 14, line 10, "recystallized" should read --recrystallized--.

UNITED STATES PATENT AND TRADEMARK OFFICE
CERTIFICATE OF CORRECTION

PATENT NO. : 4,918,207

DATED : April 17, 1990

INVENTOR(S) : Herbert C. Brown

It is certified that error appears in the above-identified patent and that said Letters Patent is hereby corrected as shown below:

Column 14, line 12, the "c" in the term beginning "(c" should be underlined.

Column 14, line 20, in the title of Example 63, "pro" should read --propane--.

Column 14, line 21, in the second line of the title of Example 63, delete "pane".

Column 14, line 32, the "c" in "(c 7.8" should be underlined.

Column 14, line 34, "128,76" should read --128.76--.

Column 14, line 47, "(Ch$_2$Cl$_2$)" should read --(CH$_2$Cl$_2$)--.

Column 14, line 48, the "c" should be underlined in the term '(c 4.8".

UNITED STATES PATENT AND TRADEMARK OFFICE
CERTIFICATE OF CORRECTION

PATENT NO. : 4,918,207

DATED : April 17, 1990

INVENTOR(S) : Herbert C. Brown

It is certified that error appears in the above-identified patent and that said Letters Patent is hereby corrected as shown below:

Column 14, line 58, in the first line of the title of Example 66, "pro" should read --propane--.

Column 14, line 59, "pane" should be deleted.

Column 14, line 63, the "c" in "(c 3," should be underlined.

Column 14, line 68, change "pro-" to --propane--.

Column 15, line 1, "pane" should be deleted.

Column 15, line 3, the "c" in the term "(c 5," should be underlined.

IN THE CLAIMS

Claim 1, the furan ring was printed incorrectly. The furan ring should be closed to read as follows:

UNITED STATES PATENT AND TRADEMARK OFFICE
CERTIFICATE OF CORRECTION

PATENT NO. : 4,918,207
DATED : April 17, 1990
INVENTOR(S) : Herbert C. Brown

It is certified that error appears in the above-identified patent and that said Letters Patent is hereby corrected as shown below:

Claim 2, line 1, delete "tet-".

Claim 2, line 2, "rahydrofuran" should read --tetrahydrofuran--.

Claim 3, line 2, "tetrahydrofurna" should read --tetrahydrofuran--.

Claim 4, line 1, delete "tet-"

Claim 4, line 2, "rahydrofuran" should read --tetrahydrofuran--.

Claim 5, line 1, delete "tet-".

Claim 5, line 2, "rahydrofuran" should read --tetrahydrofuran--.

Claim 6, line 1, delete "tet-".

Claim 6, line 2, "rahydrofuran" should read --tetrahydrofuran--.

UNITED STATES PATENT AND TRADEMARK OFFICE
CERTIFICATE OF CORRECTION

PATENT NO.  : 4,918,207
DATED       : April 17, 1990
INVENTOR(S) : Herbert C. Brown It is certified that error appears in the above-identified patent and that said Letters Patent is hereby corrected as shown below:

Claim 7, line 1, "tet-" should be deleted.

Claim 7, line 2, "rahydrofuran" should read --tetrahydrofuran--.

Claim 8, line 1, "tet-" should be deleted.

Claim 8, line 2, "rahydrofuran" should read --tetrahydrofuran.

Signed and Sealed this

Fifth Day of May, 1992

Attest:

DOUGLAS B. COMER

Attesting Officer    Acting Commissioner of Patents and Trademarks